United States Patent [19]

Kelleher et al.

[11] Patent Number: 4,931,473

[45] Date of Patent: Jun. 5, 1990

[54] ANESTHETIC ORAL COMPOSITIONS

[75] Inventors: William J. Kelleher, Storrs; William J. McClintock, Southbury, both of Conn.

[73] Assignee: Richardson-Vicks Inc., Shelton, Conn.

[21] Appl. No.: 311,155

[22] Filed: Feb. 15, 1989

[51] Int. Cl.$^5$ .............................................. A61K 31/12
[52] U.S. Cl. ...................................................... 514/688
[58] Field of Search ......................................... 514/688

[56] References Cited

U.S. PATENT DOCUMENTS

| | | | |
|---|---|---|---|
| 2,298,767 | 3/1960 | Gulesich et al. | 167/52 |
| 2,868,689 | 1/1959 | Florestane et al. | 167/52 |
| 3,231,531 | 1/1966 | Buckley et al. | 260/23 |
| 4,139,627 | 2/1979 | Lane et al. | 424/267 |
| 4,140,772 | 2/1979 | Korenowski | 423/272 |
| 4,499,108 | 2/1985 | Sequeira et al. | 514/653 |

OTHER PUBLICATIONS

Chem. Abst., 103-71005m (1985).
Chem. Abst., 107-126485h (1985).
Chemical Abstracts 84:95570g.

Primary Examiner—Stanley J. Friedman
Attorney, Agent, or Firm—David K. Dabbiere; Douglas C. Mohl; Jack D. Schaeffer

[57] ABSTRACT

Disclosed are oral anesthetic pharmaceutical compositions comprising: (a) from about 0.02% to about 25% of a pharmaceutically acceptable acid salt of a β-aminopropiophenone, such as dyclonine HCl; (b) from about 0.02% to about 20% of saccharin; and (c) from about 1% to about 99% of a pharmaceutically acceptable oral carrier. Also provided are methods for providing an anesthetic effect in humans or animals which comprises orally administering to said human or animal a safe and effective amount of these pharmaceutically compositions. Also provided is a novel process for the manufacture of anesthetic lozenges containing a β-aminopropiophenone along with saccharin.

8 Claims, No Drawings

ANESTHETIC ORAL COMPOSITIONS

TECHNICAL FIELD

The present invention relates to stable anesthetic oral pharmaceutical compositions containing β-aminopropiophenones.

BACKGROUND OF THE INVENTION

Sore throat, or pharyngitis, is the result of inflammation with pain of the throat (especially on swallowing), perceived dryness and congestion of the mucous membrane. Sore throat is a common complaint in the upper respiratory tract and can range from mild irritation to incapacitating pain.

Oral sore throat preparations, such as lozenges, sprays, solutions and the like, containing topical anesthetic/analgesic agents have long been used for the symptomatic relief of sore throat. Dyclonine HCl, a member of a class of compounds known as β-aminopropiophenones and which is chemically denoted as 3-piperidino-4'-butoxypropiophenone hydrochloride, is a well known anesthetic/analgesic agent for topical use on the mucous membranes of the mouth and throat (see Federal Register, Vol. 47, No. 101, Proposed Rules, pages 22810-13, 1982). Oral pharmaceutical compositions of dyclonine HCl commercially available in the United States include an aqueous liquid spray containing 0.1% dyclonine HCl and solid lozenges containing 1.2 mg per lozenge for children and 3.0 mg per lozenge for adults (see Physicians' Desk Reference for Non-prescription Drugs, 8th Ed., 1987, pages 518-9). The benefit of dyclonine HCl is that it provides long-acting topical anesthetic relief. The use of certain acids, particularly citric acid, to stabilize dyclonine HCl in anesthetic lozenges is reported in U.S. Pat. No. 4,139,627 to Lane et al., issued Feb. 13, 1979. In addition to its anesthetic/analgesic properties, dyclonine HCl is reported to possess antimicrobial activity. In this regard, U.S. Pat. No. 2,868,689 to Florestane et al., issued Jan. 13, 1959 discloses stabilized aqueous preparations of dyclonine HCl (0.1-5%) having topical anesthetic and antimicrobial action, the stabilization aspect being provided by the addition of chlorobutanol (0.1-0.5%).

U.S. Pat. No. 2,928,767 to Gulesich et al., issued Mar. 15, 1960 teaches the stabilization of phenothiazines (compounds totally unrelated to β-aminopropiophenones), which are subject to light-catalyzed decomposition by use of saccharin or preferably, a saccharin salt. It has now surprisingly been found that saccharin is a very satisfactory stabilizer for β-aminopropiophenones, particularly dyclonine.

It is therefore an object of the present invention to provide oral anesthetic pharmaceutical compositions comprising β-aminopropiophenones. It is a further object of the present invention to provide dyclonine-containing oral anesthetic pharmaceutical compositions which provide improved stability. It is still a further object of the present invention to provide a method of using these anesthetic pharmaceutical compositions to treat humans or animals in need of such treatment. It is still a further object of the present invention to provide a novel process for the manufacture of anesthetic lozenges.

SUMMARY OF THE INVENTION

The present invention relates to an oral anesthetic pharmaceutical composition comprising: (a) from about 0.02% to about 25% of a pharmaceutically acceptable acid salt of a β-aminopropiophenone of the formula:

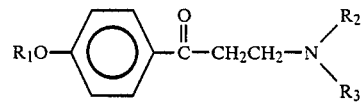

wherein $R_1$ is a $C_2$–$C_8$ alkyl, $R_2$ and $R_3$ are independently $C_1$–$C_6$ alkyl or $R_1$ and $R_2$ are $(CH_2)_n$ where n is an integer from 3 to 7; (b) from about 0.02% to about 20% of saccharin; and (c) from about 1% to about 99% of a pharmaceutically acceptable oral carrier.

Also provided are methods for providing an anesthetic effect in humans or animals which comprises orally administering to said human or animal a safe and effective amount of these pharmaceutical compositions.

Also provided is a process for the manufacture of anesthetic lozenges comprising steps of: (a) heating a candy base suitable for said composition; and (b) adding from about 0.02% to about 20% saccharin either prior to or simultaneously with the addition of from about 0.02% to about 25% of a pharmaceutically acceptable acid salt of a propiophenone of the formula:

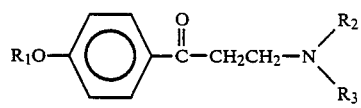

wherein $R_1$ is a $C_2$–$C_8$ alkyl, $R_2$ and $R_3$ are independently $C_1$–$C_6$ alkyl or $R_1$ and $R_2$ are $(CH_2)_n$ where n is an integer from 3 to 7.

All percentages and ratios used herein are by weight and all measurements at 25° C. unless otherwise indicated.

DETAILED DESCRIPTION OF THE DEVELOPMENT

More specifically, the present invention provides oral anesthetic pharmaceutical compositions and methods for producing anesthesia in humans or animals by administering a safe and effective amount of these same compositions, comprising:

(a) from about 0.02% to about 25% of a pharmaceutically acceptable acid salt of a β-aminopropiophenone of the formula:

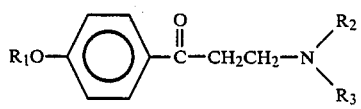

wherein $R_1$ is a $C_2$–$C_8$ alkyl, $R_2$ and $R_3$ are independently $C_1$–$C_6$ alkyl or $R_1$ and $R_2$ are $(CH_2)_n$ where n is an integer from 3 to 7;

(b) from about 0.02% to about 20% of saccharin; and (c) from about 1% to about 99% of a pharmaceutically acceptable oral carrier.

By safe and effective amount is meant that amount which provides anesthetic efficacy at a reasonable benefit/risk ratio, as is attendant with any medical treatment. Obviously, the amount of the anesthetic pharmaceutical composition which is administered will vary with such factors as the particular condition that is being treated, the severity of the condition that is being treated, the duration of the treatment, the physical condition of the patient, the nature of concurrent therapy (if any), the specific formulation and carrier employed, and the solubility and concentration of the anesthetic used.

The oral anesthetics useful in the present invention are the β-aminopropiophenones of the formula:

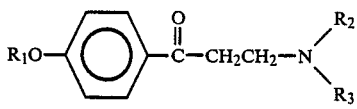

where $R_1$ is a $C_2$–$C_8$ alkyl, $R_2$ and $R_3$ are independently $C_1$–$C_6$ alkyl or $R_1$ and $R_2$ are $(CH_2)_n$ where n is an integer from 3 to 7;

Preferred propiophenones include: 3-piperidino-p-n-butoxypropiophenone, 3-piperidino-p-n-octyloxypropiophenone, 3-piperidino-p-n-ethoxypropiophenone, 3-piperidino-p-n-amoxypropiophenone, 3-piperidino-p-isobutoxypropiophenone, 3-piperidino-p-sec.-butoxypropiophenone, 3-piperidino-p-n-propoxypropiophenone, 3-piperidino-p-isoamoxypropiophenone, 3-piperidino-p-isopropoxypropiophenone, 3-piperidino-p-n-heptyloxypropiophenone, and 3-piperidino-p-n-hexyloxypropiophenone, mixtures thereof, and salts thereof.

Even more preferred propiophenones are selected from the group consisting of 3-piperidino-p-n-butoxypropiophenone and 3-piperidino-p-n-propoxypropiophenone, mixtures thereof, and salts thereof.

The most preferred propiophenone is 3-piperidino-p-n-butoxypropiophenone, and pharmaceutically acceptable salts thereof.

The hydrochloride salt of these propiophenones is preferred since it is readily available; however, other pharmaceutically acceptable salts of these compounds, such as those formed with hydrobromic acid, fumaric acid, malic acid, tartaric acid, lactic acid, adipic acid, phosophoric acid, sulfuric acid, methane sulfonic acid, naphthalene disulphonic acid, acetic acid and the like may also be utilized in a similar manner.

Saccharin, chemically denoted as 2,3-dihydroxy-3-oxobenzoisosulfonazole, has the following structure:

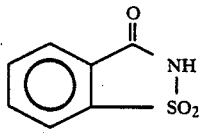

Saccharin is generally known as a non-nutritive sweetener (see Merck Index, ninth edition; Handbook of Pharmaceutical Excipients, American Pharmaceutical Association and the Pharmaceutical Society of Great Britain, 1986).

The saccharin component is present at a level of from about 0.02% to about 20.0%, preferably from about 0.03% to about 10.0%, more preferably from about 0.05% to about 1.0% and most preferably from about 0.1% to about 0.5%. Combinations of dyclonine and other conventional oral anesthetics may optionally also be used in the compositions of the present invention.

Oral anesthetic drugs suitable for use in combination with dyclonine include hexylresorcinol, aspirin, menthol, phenol, benzyl alcohol, benzocaine, butamben, dibucaine, tetracaine, butacaine, phenolate sodium, salicyl alcohol, eucalyptol, methyl salicylate and thymol, and mixtures thereof.

The most preferred optional oral anesthetic drug is phenol.

The β-aminopropiophenone and optional oral anesthetic drug are combined in a ratio of propiophenone to oral anesthetic drug of from about 1 to about 150, preferably from about 1 to about 75, and most preferably from about 1 to about 15.

Various oral dosage forms can be used, including such solid forms as tablets, capsules, granules, lozenges and bulk powders and liquid forms such as syrups, suspensions and solutions. The preferred solid oral dosage form is a lozenge or troche which can be dissolved slowly in the mouth thereby permitting the anesthetic to have a local or topical effect. Suitable methods for manufacturing such lozenges are described in U.S. Pat. No. 4,139,627 to Lane et al. issued Feb. 13, 1979. These oral forms comprise a safe and effective amount, usually at least about 0.05% of the active component. Techniques and compositions for making solid oral dosage forms are described in Marshall, "Solid Oral Dosage Forms," Modern Pharmaceutics, Vol. 7, (Banker and Rhodes, editors), 359–427 (1979), incorporated by reference herein. Techniques and compositions for making tablets (compressed, formulas and molded) and pills are described in Remington's Pharmaceutical Sciences (Arthur Osol, editor), 1553–1593 (1980), incorporated herein by reference. Solid oral dosage forms preferably contain from about 0.05% to about 95%, more preferably from about 0.01% to about 95%, and most preferably from about 25% to about 95% of the active component.

Liquid oral dosage forms include aqueous and nonaqueous solutions, emulsions, suspensions, solutions and/or suspensions reconstituted from non-effervescent granules, and can contain suitable solvents, preservatives, emulsifying agents, suspending agents, diluents, sweetening agents, coloring agents, and flavoring agents. Preferred carriers for oral administration include propylene glycol. Specific examples of pharmaceutically acceptable carriers and excipients that may be used to formulate these oral dosage forms, are described in U.S. Pat. No. 3,903,297, Robert, issued Sept. 2, 1975, incorporated by reference herein. Liquid oral dosage forms preferably contain from about 1% to about 50% and more preferably from about 1% to about 25% and most preferably from about 3% to about 10% of the active component.

In preparing the liquid pharmaceutical compositions of the present invention, the oral anesthetic drug is incorporated into an aqueous-based orally acceptable pharmaceutical carrier consistent with conventional pharmaceutical practices. An "aqueous-based orally acceptable pharmaceutical carrier" is one wherein the entire or predominant solvent content is water. Typical carriers include simple aqueous solutions, syrups, dispersions and suspensions, and aqueous based emulsions such as the oil-in-water type. While the amount of water in the compositions of this invention can vary over quite a wide range depending upon the total weight and volume of the active ingredients and other optional non-active ingredients, the total water content, based on the weight of the final composition, will generally range from about 20 to about 95%, and, preferably, from about 30 to about 95%, by weight/volume, and more preferably from about 50 to about 95%.

Although water itself may make up the entire carrier, typical formulations preferably contain a co-solvent, for example, propylene glycol, glycerin, sorbitol solution and the like, to assist solubilization and incorporation of water-insoluble ingredients, flavoring oils and the like into the composition. Such co-solvents are well known to those skilled in the art. In general, therefore, the compositions of this invention preferably contain from about 5 to about 25 volume/volume percent and, most preferably, from about 10 to about 20 volume/volume percent, of the co-solvent.

Water-insoluble or poorly soluble components may also be incorporated into aqueous-based orally acceptable pharmaceutical carriers such as dispersions, suspensions, oil-in-water emulsions and the like by means of suitable dispersing, suspending or emulsifying agents, respectively, which are readily apparent to those skilled in the art of pharmaceutical formulations.

The compositions of this invention may also optionally contain one or more other known therapeutic agents, particularly those commonly utilized in cough-/cold preparations, such as, for example, a decongestant such as pseudoephedrine hydrochloride, phenylpropanolamine HCl, phenylephrine hydrochloride and ephedrine hydrochloride; an analgesic such as acetaminophen, ibuprofen, naproxen and aspirin; an expectorant or mucolytic such as glyceryl guaiacolate, guaiacolate, terpin hydrate, ammonium chloride, N-acetylcysteine and ambroxol; and an antihistamine such as chlorpheniramine maleate, promethazine, doxylamine succinate, brompheniramine maleate and diphenhydramine hydrochloride: all of which are described in U.S. Pat. No. 4,619,934 to Sunshine et al., issued Oct. 28, 1986, which is incorporated by reference herein. Also useful are bronchodilators such as theophylline and albuterol and oral antitussive drugs. As used herein, the term "oral antitussive drug" means a drug that is taken by mouth and acts systemically to relieve cough (see Federal Register, Vol. 52, No. 155, 12 Aug. 1987, page 30055). Useful recognized oral antitussive drugs include, but are not limited to, for example, the non-narcotic types such as dextromethorphan and its acid salts, preferably the hydrobromide, noscapine, chlophedianol hydrochloride, carbetapentane citrate, caramiphen edisylate, diphenhydramine and its hydrochloride salt, fominoben, and the like, and the narcotic types such as codeine and its sulfate or phosphate salts, noscapine hydrochloride, hydrocodone and its bitartrate salt, hydromorphone hydrochloride, and the like. The usual adult dosages for such antitussives, which may also be utilized per dose in the subject compositions, are indicated in the following table:

| Oral Antitussive Drug | Usual Adult Dose (mg) |
| --- | --- |
| Dextromethorphan HBr | 10-30 |
| Chlophedianol HCl | 15-25 |
| Carbetapentane citrate | 15-30 |
| Caramiphen edisylate | 15-20 |
| Noscapine HCl | 15-30 |
| Diphenhydramine HCl | 15-25 |
| Codeine sulfate | 10-20 |
| Hydrocodone bitartrate | 5-10 |
| Hydromorphone HCl | 2 |
| Fominoben | 80-160 |

Preferred oral antitussive agents are dextromethorphan, codeine and diphenhydramine and pharmaceutically acceptable salts thereof and mixtures thereof. Even more preferred are dextromethorphan and codeine, pharmaceutically acceptable salts thereof and mixtures thereof. Most preferred is dextromethorphan and its pharmaceutically acceptable salts.

Other optional ingredients well known to the pharmacist's art may also be included in amounts generally known for these ingredients: for example, natural or artificial sweeteners, flavoring agents, colorants and the like to provide a palatable and pleasant looking final product; antioxidants, for example, butylated hydroxy anisole or butylated hydroxy toluene, and preservatives, for example, methyl or propyl paraben or sodium benzoate, to prolong and enhance shelf life.

The present invention also includes a process for the manufacture of topical anesthetic lozenges. This process comprises the steps of:
(a) heating a candy base suitable for said composition; and
(b) adding from about 0.02% to about 20% saccharin either prior to or simultaneous with the addition of from about 0.02% to about 25% of a pharmaceutically acceptable acid salt of a propiophenone of the formula:

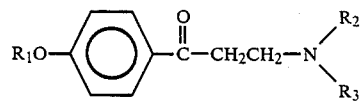

wherein $R_1$ is a $C_2$-$C_8$ alkyl, $R_2$ and $R_3$ are independently $C_1$-$C_6$ alkyl or $R_1$ and $R_2$ are $(CH_2)_n$ where n is an integer from 3 to 7;

Preferably the saccharin component is added prior to the propiophenone and comprises from about 0.05% to about 10%. Preferably, the β-aminopropiophenone component comprises from about 0.05% to about 5% of the composition.

METHOD OF TREATMENT

The present invention also encompasses methods of producing anesthesia in humans or lower animals through administering, to the human or lower animal in need of such treatment, a safe and effective amount of the pharmaceutical composition of the present invention comprising a β-aminopropiophenone along with saccharin. The amount of the pharmaceutical composition administered depends upon the percent of active ingredients within its formula, which is a function of the amount of β-aminoproiophenone and other actives required per dose, stability, release characteristics and other pharmaceutical parameters. Usually from about 0.01 mg/kg to about 10.0 mg/kg per day, preferably from about 0.01 mg/kg to about 5.0 mg/kg per day and most preferably from about 0.05 mg/kg per day to about 5.0 mg/kg per day of the pharmaceutical composition is administered as described herein. This amount can be given in a single dose or, preferably, in multiple (two or six) doses repeatedly or sustained-release dosages over the course of treatment. While dosages higher than the foregoing are effective to provide anesthetic effect, care must be taken, as with any drug, in some individuals to prevent adverse side effects.

The compositions and methods described herein are used in an art-recognized manner to provide anesthetic activity.

The following non-limiting examples illustrate embodiments of the subject invention wherein both essential and optional ingredients are combined. It is to be understood that these examples are for illustrative purposes only and are not to be construed as limiting the scope of the invention thereto.

EXAMPLE I

| A. Preparation of candy base. | | |
|---|---|---|
| Ingredients | % w/w | Quantity (g) |
| Sugar | 46.75 | 302.0 |
| Regular DE Corn Syrup | 38.25 | 247.0 |
| Water | 15.00 | 96.96 |

The ingredients were combined in a cooking pan and heated until the temperature reach 149° C. A portion of this molten mass was allowed to cool and solidify for use as salvage.

B. Preparation of the lozenge composition with simultaneous addition of the stabilizer.

| Ingredients | % w/w | Quantity (g) |
|---|---|---|
| Dyclonine hydrochloride | 0.130 | 0.585 |
| Salvage Candy Base* | 5.000 | 22.500 |
| Stabilizer | (see table below) | |
| Candy Base q.s. to | 100% | 450.000 g |

The molten candy base was poured into a stainless steel beaker. The dyclonine hydrochloride and stabilizer (saccharin or citric acid) previously combined and triturated with the salvage candy base, were added to the molten candy base at the end of the heating period and the mixture was stirred. Just prior to solidification, the mixture was poured onto a cooling slab. The hardened lozenge composition was analyzed for dyclonine by HPLC. Recoveries of dyclonine for compositions containing no stabilizer and concentrations of saccharin or citric acid ranging from 0.10% to 0.30% by weight are shown in the table below.

| Concentration of Stabilizer | Recovery of Dyclonine (%) | |
|---|---|---|
| % w/w | Saccharin | Citric Acid |
| 0.00 | 55.8 | 55.8 |
| 0.10 | 94.3 | 86.5 |
| 0.20 | 96.4 | 91.6 |
| 0.30 | 95.0 | 92.3 |

These data demonstrate that saccharin is not only an effective stabilizer of dyclonine, but is superior to citric acid when used in the same concentrations.

EXAMPLE II

| A. Preparation of the lozenge composition with prior addition of stabilizer. | | |
|---|---|---|
| Ingredients | % w/w | Quantity (g) |
| Dyclonine hydrochloride | 0.130 | 0.585 |
| Salvage candy base | 5.000 | 22.50 |
| Stabilizer | (see table below) | |
| Candy base q.s. to | 100% | 450.00 |

The stabilizer was triturated with one-half the quantity of salvage candy base, and the dyclonine was triturated with the other half. The stabilizer-salvage mixture was added to the candy base at 145° C. on the heating leg of the cycle. Heating was discontinued when the temperature of the mixture reached 149° C. The dyclonine hydrochloride-salvage mixture was then added to the molten candy base containing stabilizer. The mixture was stirred, and was poured onto a cooling slab just prior to solidification. Recoveries of dyclonine were determined by HPLC. The recovery values for compositions containing no previously added stabilizer and for compositions containing concentrations of saccharin or citric acid ranging from 0.10% to 0.40% by weight are given in the table below.

| Concentration of Stabilizer | Recovery of Dyclonine (%) | |
|---|---|---|
| % w/w | Saccharin | Citric Acid |
| 0.00 | 55.8 | 55.8 |
| 0.10 | 86.1 | 74.4 |
| 0.20 | 82.6 | 76.5 |
| 0.40 | 96.7 | 93.5 |

These data demonstrate that saccharin is not only an effective stabilizer of dyclonine, but is superior to citric acid when used in the same concentrations.

EXAMPLE III

| A lozenge is made as follows | |
|---|---|
| Ingredients | Amount |
| Sucrose | 1237.5 mg |
| Corn Syrup, Regular DE | 1012.5 mg |
| Phenol | 32.5 mg |
| Dyclonine HCl | 3.0 mg |
| Saccharin | 9.2 mg |
| Flavorant | 4.6 mg |
| Colorant | 0.7 mg |
| | 2300.0 mg |

Colorant is mixed with 396.4 mg of purified water. The sucrose and corn syrup are added to this mixture, which is then cooked to 149° C. Dyclonine hydrochloride and saccharin are mixed into the cooked candy base. When this mixture cools to 130° C., phenol is added as a 90% w/w solution and mixed in. Flavorant is mixed in immediately after. The resulting molten material is formed into a 2.3 gram lozenge.

Substantially similar results are obtained when the dyclonine HCl is replaced, in whole or in part, with 3-piperidino-p-n-butoxypropiophenone, 3-piperidino-p-n-octyloxypropiophenone, 3-piperidino-p-n-ethoxypropiophenone, 3-piperidino-p-n-amoxypropiophenone, 3-piperidino-p-isobutoxypropiophenone, 3-piperidino-p-sec.-butoxypropiophenone, 3-piperidino-p-n-propoxypropiophenone, 3-piperidino-p-isoamoxypropiophenone, 3-piperidino-p-isopropoxypropiophenone, 3-piperidino-p-n-heptyloxypropiophenone, and 3-piperidino-p-n-hexyloxypropiophenone, mixtures thereof, and salts thereof.

EXAMPLE IV

A stable liquid composition for oral administration is prepared by combining the following ingredients:

| Ingredients | % w/v | |
|---|---|---|
| Ethanol (95%) | 13.200 | v/v |
| Propylene Glycol | 20.000 | v/v |
| Glycerin | 10.000 | |
| Sorbitol Solution, 70% | 8.600 | |
| Saccharin | 0.130 | |
| Dyclonine Hydrochloride | 0.100 | |
| Flavorant | 0.400 | |
| Colorant | 0.010 | |

-continued

| Ingredients | | % w/v |
|---|---|---|
| Water, Purified | q.s. to | 100.000 |

3.5 milliliters of this liquid is administered to a human in need of treatment, by, for example, spraying directly on the afflicted area, thereby providing anesthetic relief.

EXAMPLE V

A stable liquid composition for oral administration is prepared by combining the following ingredients

| Ingredients | | % w/v |
|---|---|---|
| Ethanol (95%) | | 13.200 v/v |
| Propylene Glycol | | 20.000 v/v |
| Glycerin | | 10.000 |
| Sorbitol Solution, 70% | | 8.600 |
| Saccharin | | 0.130 |
| Phenol | | 1.400 |
| Dyclonine Hydrochloride | | 0.100 |
| Flavorant | | 0.400 |
| Colorant | | 0.010 |
| Water, Purified | q.s. to | 100.000 |

3.5 milliliters of this liquid is administered to a human in need of treatment, by, for example, spraying directly on the afflicted area, thereby providing anesthetic relief.

What is claimed is:

1. A method of stabilizing oral anesthetic pharmaceutical compositions containing a β-aminopropiophenone which comprises adding to said compositions a stabilizing amount of saccharin.

2. A method according to claim 1 wherein said stabilizing amount of saccharin ranges from about 0.02% to about 20%.

3. A stabilized oral anesthetic composition comprising:
   (a) from about 0.02% to about 25% of a pharmaceutically acceptable acid salt of a β-amino propiophenone of the formula:

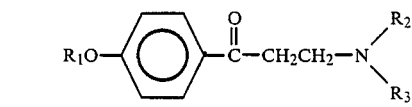

wherein $R_1$ is a $C_2$-$C_8$ alkyl, $R_2$ and $R_3$ are independently $C_1$-$C_6$ alkyl or $R_1$ and $R_2$ are $(CH_2)_n$ where n is an integer from 3 to 7;
   (b) from about 0.02% to about 20% of saccharin; and
   (c) from about 1% to about 99% of a pharmaceutically acceptable oral carrier.

4. An oral anesthetic pharmaceutical composition according to claim 3 which comprises from about 0.05% to about 10% of saccharin and which comprises from about 0.05% to about 5.0% of the propiophenone.

5. An oral anesthetic composition according to claim 4 wherein said propiophenone is selected from the group consisting of 3-piperidino-p-n-butoxypropiophenone, 3-piperidino-p-n-octyloxypropiophenone, 3-piperidino-p-n-ethoxypropiophenone, 3-piperidino-p-n-amoxypropiophenone, 3-piperidino-p-isobutoxypropiophenone, 3-piperidino-p-sec.-butoxypropiophenone, 3-piperidino-p-n-propoxypropiophenone, 3-piperidino-p-isoamoxypropiophenone, 3-piperidino-p-isopropoxypropiophenone, 3-piperidino-p-n-heptyloxypropiophenone, and 3-piperidino-p-n-hexyloxypropiophenone, mixtures thereof, and salts thereof.

6. An oral anesthetic composition according to claim 5 which comprises from about 0.05% to about 1.0% of saccharin and wherein the propiophenone is selected from the group consisting of 3-piperidino-p-n-butoxypropiophenone and 3-piperidino-p-n-propoxypropiophenone, mixtures thereof, and salts thereof.

7. An oral anesthetic composition according to claim 6 wherein the propiophenone is 3-piperidino-p-n-butoxypropiophenone, and pharmaceutically acceptable salts thereof.

8. An oral anesthetic composition according to claim 7 wherein the propiophenone is the hydrochloride salt of 3-piperidino-p-n-butoxypropiophenone.

* * * * *